United States Patent
Schaller et al.

(10) Patent No.: US 7,515,680 B2
(45) Date of Patent: Apr. 7, 2009

(54) METHOD FOR CORRECTING DETECTOR SIGNALS OF A UNIT FOR RECONSTRUCTING TOMOGRAMS FROM PROJECTION DATA

(75) Inventors: Andreas Schaller, Erlangen (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 393 days.

(21) Appl. No.: 11/180,723

(22) Filed: Jul. 14, 2005

(65) Prior Publication Data
US 2006/0013359 A1 Jan. 19, 2006

(30) Foreign Application Priority Data
Jul. 15, 2004 (DE) .......... 10 2004 034 237

(51) Int. Cl.
*G01N 23/06* (2006.01)
(52) U.S. Cl. ........................... 378/19; 378/207
(58) Field of Classification Search ............ 378/19, 378/98.8, 207; 250/252.1, 369, 370.09, 207; 250/363.09; 382/128–131
See application file for complete search history.

(56) References Cited

U.S. PATENT DOCUMENTS

| | | | | |
|---|---|---|---|---|
| 4,225,789 A * | 9/1980 | Albrecht | .......... | 378/5 |
| 5,528,649 A | 6/1996 | Heidsieck | | |
| 5,680,427 A * | 10/1997 | Dobbs et al. | .......... | 378/19 |
| 5,828,719 A * | 10/1998 | He et al. | .......... | 378/4 |
| 5,867,553 A | 2/1999 | Dobbs et al. | | |
| 6,148,057 A * | 11/2000 | Urchuk et al. | .......... | 378/18 |
| 6,529,575 B1 * | 3/2003 | Hsieh | .......... | 378/4 |
| 2002/0064254 A1 * | 5/2002 | Aoki et al. | .......... | 378/98.7 |
| 2004/0109528 A1 * | 6/2004 | Nukui et al. | .......... | 378/19 |

OTHER PUBLICATIONS

Kumar et al., A mixed approach to artifacts minimization in a continuous-rotate X-ray based tomographic imaging system using linear detector array, 2002, Applied Radiation and Isotopes, 55, pp. 543-555.*
Rivers, Tutorial Introduction to X-ray Computed Microtomography Data Processing, May 14, 1998, accessible online at http://www-fp.mcs.anl.gov/xray-cmt/rivers/tutorial.html.*
K. Briess, S. Hilbert, B. Kirchner: "Analoge Echtzeitvorverarbeitung von WAOSS-Sensersignalen"; Bild und Ton Bd. (1992), Heft 9/10, Seite 231-239, English translation, PTO-07-3982.*
K.Brieβ, S.Hilbert, B.Kirchner: "Analoge Echtzeitvorverarbeitung von WAOSS-Sensorsignalen"; Bild und Ton Bd.45 (1992), Heft 9/10,Seite 231-239.

* cited by examiner

*Primary Examiner*—Edward J Glick
*Assistant Examiner*—John M Corbett
(74) *Attorney, Agent, or Firm*—Harness, Dickey & Pierce, P.L.C.

(57) ABSTRACT

A method is proposed for correcting detector signals of a unit for reconstructing tomograms from projection data, in particular of a computer tomography unit, of a ray detector having a multiplicity of individual detector channels that form the projection data, attenuation values of individual X-rays being calculated after the passage through an examination object. In order to reconstruct the tomograms from attenuation values of the X-rays, the detector output signals are subjected to a nonlinearity correction before the calculation of the attenuation values.

9 Claims, No Drawings

METHOD FOR CORRECTING DETECTOR SIGNALS OF A UNIT FOR RECONSTRUCTING TOMOGRAMS FROM PROJECTION DATA

The present application hereby claims priority under 35 U.S.C. §119 on German patent application number DE 10 2004 034 237.7 filed Jul. 15, 2004, the entire contents of which is hereby incorporated herein by reference.

FIELD

The invention generally relates to a method for correcting detector signals. More particularly, it relates to a method for correcting detector signals of a unit for reconstructing tomograms from projection data, in particular of a computer tomography unit, of a ray detector having a multiplicity of individual detector channels that form the projection data, attenuation values of individual X-rays being calculated after the passage through an examination object.

BACKGROUND

Both in computer tomography and in all other methods that reconstruct tomograms from projection data, it is important that the detectors used to measure irradiation scanning an examination object exhibit as linear as possible a response to the detected radiation. Nonlinearities, in particular those that differ from measurement channel to measurement channel, lead to ring artifacts in the reconstructed image, and disturb the image quality.

This problem is addressed in the prior art both by using expensive detectors with high linearity, and by applying corrections to the already calculated attenuation values of the measured radiation.

SUMMARY

It is an object of an embodiment of the invention to propose an improved correction method that permits the use of simpler detectors without suffering a loss in quality in the image recordings.

The inventors have recognized that information is lost in the case of the previously known correction methods, in which the corrections are undertaken on the attenuation values of the radiation that have already been calculated with the aid of the uncorrected detector output data. Although the attenuation values do include the information relating to the object attenuation—which effects a spectral variation in the radiation—, for which reason it is also possible to correct spectral nonlinearities that are based on the different response of the individual detector channels to spectral differences, the information relating to the actual detector signal is, however, no longer present. Thus, it is not possible to detect the variation in the attenuation that was measured for various X-ray dose rates or the tube currents coupled thereto, since the necessary information is no longer included in the attenuation values.

In other words, since the attenuation values reflect merely the ratio of two values, specifically of the intensity $I_0$ of the radiation without examination object to the intensity $I$ of the attenuated radiation after the passage through the examination object, the information relating to the intensity of the radiation, that is to say the dose rate, is no longer present per se. Correspondingly, it is also impossible to correct nonlinearities caused there.

However, this problem can be solved by correcting the detector data as early as before the calculation of the attenuation coefficients. The correction thus takes place not on the value of the ratio $I/I_0$, but already comes in at the measured intensity $I$ of the detector channels or the detector elements of the detector.

Consequently, the inventors propose to improve the method in at least one embodiment for correcting detector signals of a unit for reconstructing tomograms from projection data, in particular of a computer tomography unit, of a ray detector having a multiplicity of individual detector channels that form the projection data, attenuation values of individual X-rays being calculated after the passage through an examination object, to the effect that in order to reconstruct the tomograms from attenuation values of the X-rays, the detector output signals are subjected to a nonlinearity correction before the calculation of the attenuation values.

It is advantageously possible for the purpose of the nonlinearity correction of the detector channels in at least one embodiment, for correction factors to be determined with reference to their spectral dependence and with reference to their dependence on the signal intensity. It is preferably possible in order to determine the spectral dependence and the dependence on the signal intensity of the correction factors, for the error behavior of each detector element to be calculated as a function of a monitor value of the dose rate and of the signal strength of the respective detector element.

Use may be made, in at least one embodiment, of the fact that there is a functional dependence of the monitor value of the dose rate on the intensity of radiation impinging on a detector element, on the one hand, and at the same time also a relationship between the variation in the radiation spectrum—radiation hardening—and the variation in intensity of the radiation downstream of the penetrated object in conjunction with an identical monitor value, on the other hand. Thus, the consideration of monitor value and signal strength of a detector element supplies a conclusion on the fraction of the spectrally-induced correction factor and of the correction factor induced by signal strength, such that it is thereby possible to carry out a correction of nonlinearity with particular accuracy. For example, a radiation detector fitted at the edge and not influenced by the object to be scanned, or else a simple tube current measurement can serve as monitor value for the dose rate.

In order to determine these correction factors for the nonlinearity correction of the detector channels in at least one embodiment, it is furthermore proposed to carry out measurements with the aid of different tube currents and of smooth measurement phantoms of different thickness inserted into the beam path so as to yield measurement series that have different signal strengths for different dose rates, on the one hand, and different radiation spectra, on the other hand, from which the correction factors dependent on signal strength and dependent on spectrum can be calculated.

It is fundamentally possible in this case to determine the error behavior of the output signal of the detector elements of a detector as a function both of the signal intensity and of the measured radiation spectrum on the basis of a sufficiently large number of measurements and on the basis of a multiplicity of detector elements that are subjected to the same radiation.

In an advantageous design of the method according to at least one embodiment of the invention, the inventors also propose to correct the detector output data with the aid of at least the following method steps in the specified sequence:

Carrying out an air calibration,
Carrying out the nonlinearity correction,
Carrying out a monitor standardization,
Carrying out a channel correction.

In addition, it is also possible to carry out a logarithmization of the measured values before the abovenamed method steps.

It is advantageous, furthermore, when the nonlinearity correction is performed using the following formula:

$$L = F(G(S-S_0) - M + M_0)$$

with the attenuation value (=line integral) L, the function F for correcting spectral nonlinearities, and the function G for correcting nonlinearities dependent on signal, $S = -\ln(s)$, $S_0 = -\ln(s_0)$, $M = -\ln(m)$, $M_0 = -\ln(m_0)$ s corresponding to the signal of a channel, $s_0$ to the signal of a channel during air measurement, m to a monitor signal, and $m_0$ to a monitor signal during air measurement.

One advantage of the above-described correction methods in at least one embodiment, which already start with the actual detector signal, resides in that it is also possible to correct relatively large signal nonlinearities, and even nonlinearities dependent on dose rate can be corrected. Detector elements that are substantially more cost effective can thereby now be used without loss of image quality.

DETAILED DESCRIPTION OF THE EXAMPLE EMBODIMENTS

At least one embodiment of the invention is described in more detail below with the aid of a model, the following notation that lower case letters stand for linear values such as signals and currents, and upper case letters stand for logarithmic variables such as attenuation values being valid in the formulae subsequently specified.

The starting point is a model of an ideal system $$\frac{s}{m} = \frac{s_0}{m_0} \exp(-L). \tag{1}$$

Here, s is the signal of a channel, m the monitor signal, $s_0$ and $m_0$ signal and monitor signal in the air scan and L the attenuation value (line integral). The following equation results from logarithmization:

$$S - S_0 = M - M_0 + L. \tag{2}$$

Here, $S = -\ln s$, $M = -1$ nm, etc. The non-ideal system can be represented as follows:

$$S - S_0 = G^{-1}(M - M_0 + F^{-1}(L)). \tag{3}$$

The two functions F and G in this case model different aspects of the nonlinearity:

F. varies the attenuation value and models spectral nonlinearities.

G varies the signal value and models signal nonlinearities.

The aim of the preprocessing of the signal values is to determine the line integral L. If the functions F and G are known, the equation (3) can be solved for L:

$$L = F(G(S-S_0) - M + M_0). \tag{4}$$

In this equation, the most important preprocessing steps include:

1. Air calibration: $S_{air} = S - S_0$
2. Nonlinearity correction (NLC): $S_{nlc} = G(S_{air})$
3. Monitor standardization: $S_{mon} = S_{nlc} - M + M_0$
4. Channel correction (CCR): $L = F(S_{mon})$ The correction functions F and G are now determined as follows:

It is assumed that measured data are present for various tube currents $I_i$ and line integrals $L_k$, the channel index being suppressed:

$$S_{ik} - S_0 = G^{-1}(M_i - M_0 + F^{-1}(L_k)) \tag{5}$$

As in the case of the channel correction, the aim now is to process the correction only differentially. It is therefore expedient to calculate the (negative) deviation that is yielded from a highpass filtering of the data vectors along the channel direction:

$$\delta(S_{ik} - S_0) = \text{smooth}(S_{ik} - S_0) - (S_{ik} - S_0). \tag{6}$$

The task can therefore be reformulated in the following way:

Search for functions F and G such that the equations $$F(G(S_{ik} - S_0) - M_i + M_0) - (S_{ik} - S_0 - M_i + M_0) = \delta(S_{ik} - S_0) \tag{7}$$

are satisfied as possible for all (i, k).

The functions F and G can expediently be parameterized as a linear combination of single terms:

$$F(X) = X + \sum_s f_s F_s(X) \tag{8}$$

$$G(X) = X + \sum_t g_t G_t(X).$$

The coefficients $f_s$ and $g_t$ are to be determined for each channel. The optimization of equation (7) is particularly simple when it is assumed that the coefficients $f_s$ and $g_t$ are small numbers and equation (7) is linearized on this basis:

$$\sum_s f_s F_s(S_{ik} - S_0 - M_i + M_0) + \sum_t g_t G_t(S_{ik} - S_0) = \delta(S_{ik} - S_0). \tag{9}$$

The minimization of the error sums $$\sum_{ik} \frac{1}{\sigma_{ik}^2} \left( \sum_s f_s F_s(S_{ik} - S_0 - M_i + M_0) + \sum_t g_t G_t(S_{ik} - S_0) - \delta(S_{ik} - S_0) \right)^2, \tag{10}$$

in which $\sigma_{ik}$ denotes the statistical dispersion of the measured value, then leads for each detector channel to a linear equation for the coefficients $f_s$ and $g_t$:

$$\begin{pmatrix} \langle FF \rangle & \langle FG \rangle \\ \langle GF \rangle & \langle GG \rangle \end{pmatrix} \begin{pmatrix} f \\ g \end{pmatrix} = \begin{pmatrix} \langle F\delta \rangle \\ \langle G\delta \rangle \end{pmatrix} \tag{11}$$

it being necessary to form the submatrices from the sums $$\langle FF \rangle_{s_1 s_2} = \sum_{ik} \frac{1}{\sigma_{ik}^2} F_{s_1}(S_{ik} - S_0 - M_i + M_0) F_{s_2}(S_{ik} - S_0 - M_i + M_0) \tag{12}$$

$$\langle FG \rangle_{st} = \langle GF \rangle_{ts} = \sum_{ik} \frac{1}{\sigma_{ik}^2} F_s(S_{ik} - S_0 - M_i + M_0) G_t(S_{ik} - S_0)$$

$$\langle GG \rangle_{t_1 t_2} = \sum_{ik} \frac{1}{\sigma_{ik}^2} G_{t_1}(S_{ik} - S_0) G_{t_2}(S_{ik} - S_0)$$

$$\langle F\delta \rangle_s = \sum_{ik} \frac{1}{\sigma_{ik}^2} F_s(S_{ik} - S_0 - M_i + M_0) \delta(S_{ik} - S_0)$$

$$\langle G\delta \rangle_t = \sum_{ik} \frac{1}{\sigma_{ik}^2} G_t(S_{ik} - S_0) \delta(S_{ik} - S_0).$$

The following set of correction terms has proved itself in simulations:

$$F_1(X)=X$$
$$F_2(X)=X^2 \quad (13)$$
$$G_1(X)=X$$
$$G_2(X)=X^2$$
$$G_3(X)=\exp(X). \quad (14)$$

The F terms correspond precisely to the known channel correction with the linear and quadratic fractions; it is recommended in the case of the G terms to take account if appropriate of an exponential term, that is to say one proportional to signal, with the aid of which it is also possible to model relatively large deviations in conjunction with very small signals, for example an additive offset.

On the basis of the described method for the correction of nonlinearities, in the case of which the spectrally-induced effects and the effects induced by signal levels can be separated for the first time, a substantially more effective correction is possible which now also permits a lesser demand to be placed on the linearity and uniformity of the detector elements used without having to accept losses in quality when compiling images.

It is self-evident that the abovenamed features of the invention can be used not only in the respectively specified combination, but also in other combinations or on their own without departing from the scope of the invention.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for correcting detector signals of a unit for reconstructing tomograms from projection data of a ray detector including a multiplicity of individual detector channels that form the projection data, the method comprising:
   calculating error behavior of each detector element as a function of a monitor value of a dose rate and of a signal strength of a respective detector element;
   determining correction factors with reference to spectral dependence and dependence on signal intensity;
   subjecting the detector output signals to a nonlinearity correction based on the determined correction factors before a calculation of attenuation values;
   calculating the attenuation values of individual rays after passage through an examination object; and
   reconstructing the tomograms based on the calculated attenuation values.

2. The method as claimed in the preceding patent claim 1, wherein, in order to determine the correction factors for nonlinearity correction of the detector channels, measurements are carried out based on different tube currents and of smooth measurement phantoms of different thickness inserted into a beam path, and the errors of individual detector elements relative to a smoothed mean value of adjacent detector elements are calculated for different dose rates and for different radiation spectra.

3. The method as claimed in claim 1, wherein detector output data are corrected with the aid of the following steps in the specified sequence:
   carrying out an air calibration;
   carrying out the nonlinearity correction;
   carrying out a monitor standardization; and
   carrying out a channel correction.

4. The method as claimed in claim 3, wherein a logarithmization of the measured values is carried out as a first step.

5. The method as claimed in claim 1, wherein the nonlinearity correction is performed using the following formula:

$$L=F(G(S-S_0)-M+M_0)$$

with the attenuation value L, the function F for correcting spectral nonlinearities, and the function G for correcting nonlinearities dependent on signal strength, $S=-\ln(s)$, $S_0=-\ln(s_0)$, $M=-\ln(m)$, $M_0=-\ln(m_0)$, s corresponding to the signal of a channel, $s_0$ to the signal of a channel during air measurement, m to a monitor signal, and $m_0$ to a monitor signal during air measurement.

6. A computer storage medium storing a program, which when executed on a computer, causes the computer to carry out the method as claimed in claim 1.

7. A method for correcting detector signals of a unit for reconstructing tomograms from projection data of a ray detector including a multiplicity of individual detector channels that form the projection data, the method comprising:
   calculating error behavior of each detector element as a function of a monitor value of a dose rate and of a signal strength of the respective detector element to determine spectral dependence and dependence on signal intensity;
   determining correction factors of detector channels with reference to their spectral dependence and their dependence on signal intensity;
   subjecting detector output signals to a nonlinearity correction based on the determined correction factors before a calculation of attenuation values;
   calculating attenuation values of individual rays after passage through an examination object, wherein the tomograms are reconstructable from the calculated attenuation values of the rays; and
   reconstructing the tomograms based on the calculated attenuation values.

8. The method as claimed in claim 7, wherein the nonlinearity correction is performed using the following formula:

$$L=F(G(S-S_0)-M+M_0)$$

with the attenuation value L, the function F for correcting spectral nonlinearities, and the function G for correcting non linearities dependent on signal strength, $S=-\ln(s)$, $S_0=-\ln(s_0)$, $M=-\ln(m)$, $M_0=-\ln(m_0)$, s corresponding to the signal of a channel, $s_0$ to the signal of a channel during air measurement, m to a monitor signal, and $m_0$ to a monitor signal during air measurement.

9. A computer readable medium storing a computer program, which when run on a computer, cause the computer to carry out the method as claimed in claim 7.

* * * * *